US00PP33321P2

(12) United States Plant Patent
Janßen

(10) Patent No.: US PP33,321 P2
(45) Date of Patent: Aug. 3, 2021

(54) FARGESIA PLANT NAMED 'JAN W2M'

(50) Latin Name: ***Fargesia* hybrid**
Varietal Denomination: JAN W2M

(71) Applicant: Wilfried Janßen, Edewecht (DE)

(72) Inventor: Wilfried Janßen, Edewecht (DE)

( * ) Notice: Subject to any disclaimer, the term of this patent is extended or adjusted under 35 U.S.C. 154(b) by 0 days.

(21) Appl. No.: 17/009,600

(22) Filed: Sep. 1, 2020

(51) Int. Cl.
*A01H 5/12* (2018.01)
*A01H 6/00* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
(74) *Attorney, Agent, or Firm* — Penny J. Aguirre

(57) ABSTRACT

A new cultivar of *Fargesia* plant named 'JAN W2M' that is characterized by its short plant height, its leaves that are small in size and dark green in color.

2 Drawing Sheets

Botanical classification: *Fargesia* hybrid.
Variety denomination: 'JAN W2M'.

CROSS REFERENCE TO A RELATED APPLICATIONS

This application is co-pending with a U.S. Plant Patent Application filed for a plant derived from the same breeding program that is entitled *Fragesia* Plant Named 'JAN W3M' (U.S. Plant patent Ser. No. 17/009,617). This application is also related to a European plant breeders' rights application filed on Jul. 31, 2017, application No. 2017/1895. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Fargesia* of hybrid origin and will be referred to hereafter by its cultivar name, 'JAN W2M' . 'JAN W2M' is a new cultivar of bamboo shrub grown for use as a landscape plant.

'JAN W2M' was selected as a single unique plant by the Inventor in a trial field in Edewecht, Germany in 2014 (with numerous seedlings evaluated from 2008 to 2014). The trial field had been planted with seeds from an open pollinated plant of an unnamed and unpatented plant of *Fargesia murieliae* x *Fargesia nitida* from the Inventor's breeding program. The exact male parent is unknown as the seeds were set after open pollination.

Asexual propagation of the new cultivar was first accomplished by the inventor using division in 2014 in Edewecht, Germany. Asexual propagation by division has been determined that the characteristics of 'JAN W2M' are stable and reproduced true to type in successive generations.

SUMMARY OF THE INVENTION

The following traits have been repeatedly observed and represent the characteristics of the new cultivar. These attributes in combination distinguish 'JAN W2M' as a unique cultivar of *Fargesia*.

1. 'JAN W2M' exhibits a short plant height.
2. 'JAN W2M' exhibits leaves that are small in size.
3. 'JAN W2M' exhibits leaves that are dark green in color.

The female plant of 'JAN W2M' differs from 'JAN W2M' in having a shorter plant height, leaves that are larger in size and leaves that are lighter green in color. Typical plant of *Fragesia murieliae* x *Fragesia nitida* differs from 'JAN W2M' in having a much taller plant height. 'JAN W2M' can be most closely compared to the cultivars 'Jan 108' (not patented), and 'Jumbo' (not patented), and 'JAN W3M'. 'Jan 108' differs from 'JAN W2M' in having a taller plant height, more vigorous growth habit, and leaves that are larger in size and lighter green in color. 'Jumbo' differs from 'JAN W2M' in having a more vigorous plant habit, a taller and wider plant size, leaves that are larger in size and lighter green in color, and in not responding as well to pruning. 'JAN W3M' differs from 'JAN W2M' in being more compact with a smaller plant height and width.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantago, Zentralverband Gartenbau e.V and other sites presenting its entrance in the new product showcase at the International Plant Fair "IPM Essen", Bambus Borse, Bambus Heppingsen, Bambus Hecken, Well-born Bamboo Africa, Taspo, Garten & FreizeitMarkt, Gabot, Bambus-Versand, Ambusudsalg, Bambus vom Limhorn, Helmers Baumschulen GmgH, Fargesia Der Gartenbambus, and Bambuswald.

BRIEF DESCRIPTION OF THE DRAWINGS

The accompanying colored photographs illustrate the overall appearance and distinct characteristics of the new

*Fargesia*. The photographs were taken of a 2-year-old plant as grown outdoors in a polyethylene tunnel in a 70-cm container in Edewecht, Germany.

Figure 1:
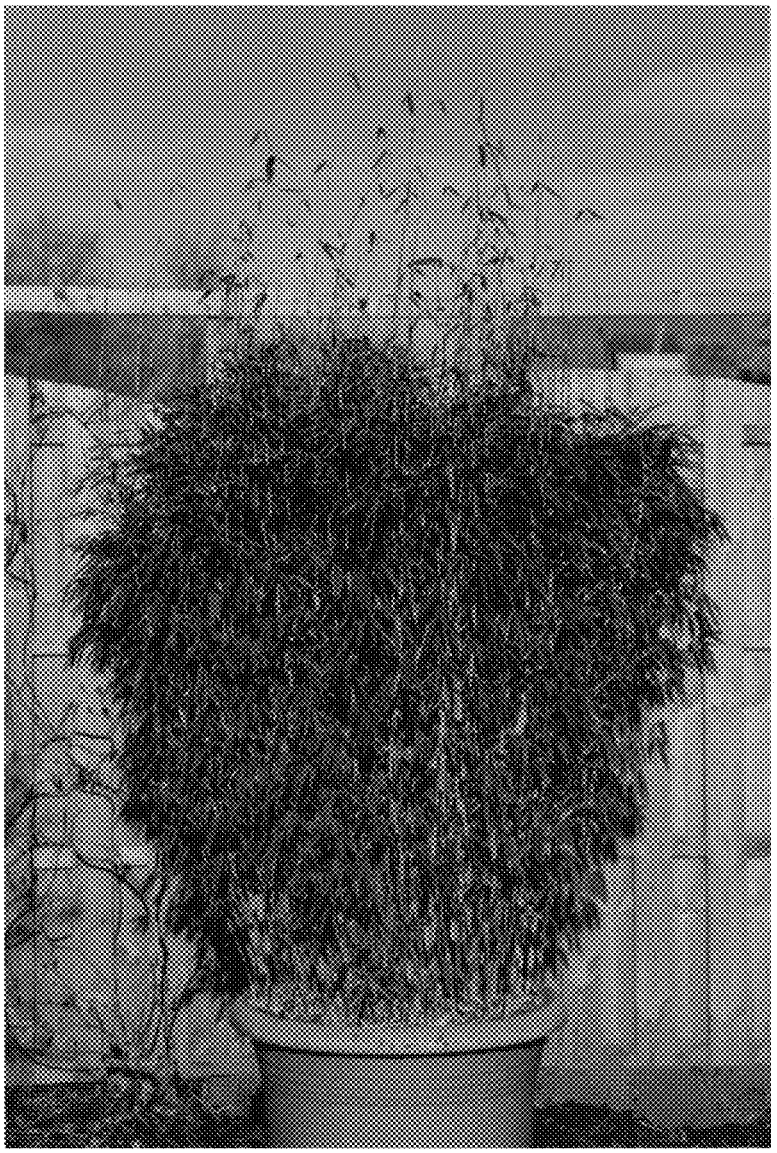

The photograph in FIG. 1 illustrates the plant habit of 'JAN W2M'.

Figure 2:
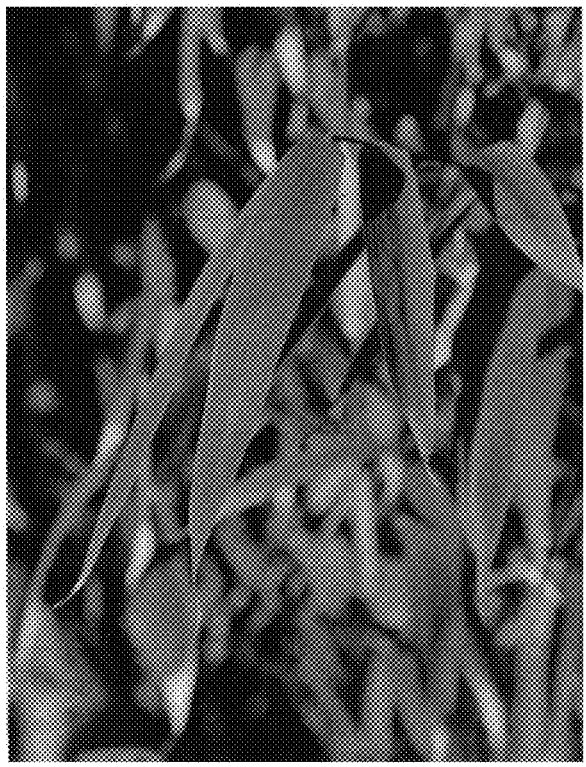

The photograph in FIG. 2 provides a close-up view of the foliage of 'JAN W2M'.

Figure 3:
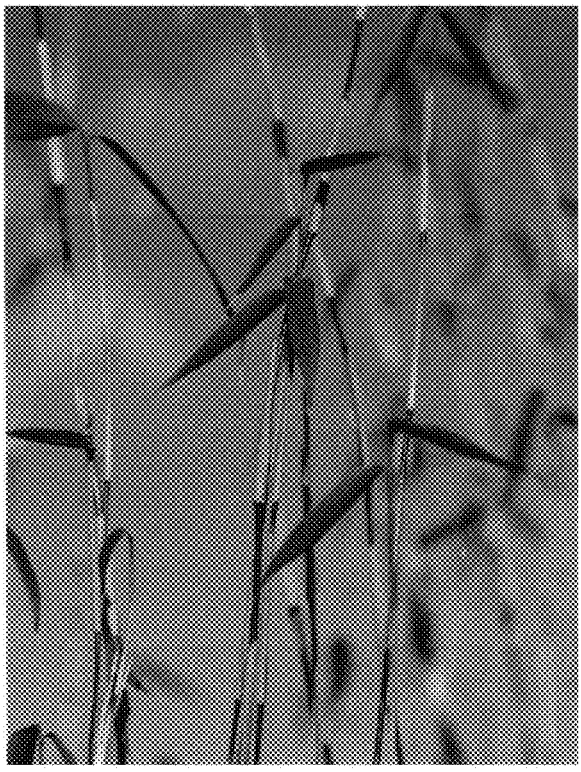

The photograph in FIG. 3 provides a close-up view of the main shoots of 'JAN W2M'.

The colors in the photographs are as close as possible with the digital photography techniques utilized and the color values cited in the detailed botanical description accurately describe the colors of the new *Fargesia*.

DETAILED BOTANICAL DESCRIPTION

The following is a description of 2-year-old plants as grown outdoors in a polyethylene tunnel in 70-cm containers in Edewecht, Germany. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Perennial bamboo.

*Plant habit*.—Short, obovate in shape, upright stems with dense foliage.

*Height and spread*.—Reaches an average of 2 m in height 1.5 m in width when mature in the landscape.

*Cold hardiness*.—At least in U.S.D.A. Zone 5.

*Diseases and pests*.—No resistance or susceptibility to diseases or pests has been observed.

*Root description*.—Fibrous, 199D in color.

*Propagation*.—Division.

*Growth rate*.—Moderate to vigorous.

*Root development*.—Approximately 1 month after division to root into a small container and 26 weeks from propagation to produce a saleable plant.

Stem description:

*Stem shape*.—Rounded.

*Stem strength*.—Very strong.

*Stem color*.—Young stems; 200A, mature stems; 146B, internodes; 146B, scale leaf scars a color between199C and N199C, older stems and bark; 152C.

*Stem size*.—Main branches; average of 131.3 cm in length, 4.5 mm in diameter, internodes slightly thicker measuring 5 mm in diameter.

*Stem surface*.—Moderately glossy, partly matte due to a thin waxy layer between 188C and 198C in color.

*Stem aspect*.—Near vertical, an average of 85° to horizontal.

*Internode length*.—7 cm.

*Branching*.—An average of 700 main branches per plant, no lateral branches present.

*Scale leaves*.—Young stems have scale leaves that are dropped as the stems mature; oblanceolate in shape, average of 7 cm in length and 1.7 cm in width, obtuse apex, cuneate base, upper surface (inner) color; 199C, lower (outer) surface color; between 165B and N167A.

Foliage description:

*Leaf shape*.—Lanceolate.

*Leaf division*.—Simple.

*Leaf arrangement*.—Alternate, growing at the tips of main and lateral branches.

*Leaf attachment*.—Petiolate.

*Leaf base*.—Cuneate.

*Leaf apex*.—Narrow long apiculate.

*Leaf venation*.—Parallel, upper surface color; 144A, lower surface color; 138B.

*Leaf margins*.—Entire.

*Leaf surface*.—Both surfaces smooth, glabrous, non-rugose, upper surface slightly glossy, lower surface matte.

*Leaf size*.—Average of 6.8 cm in length and 1.1 cm in width.

*Leaf color*.—Young upper surface; 141B and 143A, young lower surface; 138A, mature upper surface; NN137B, mature lower surface NN137D.

*Quantity*.—An average of 4 (varying between 3 and 5) per branch.

*Petioles*.—Average of 2.5 mm in length and 1 mm in diameter, both surfaces are smooth and glabrous with upper surface moderately glossy and lower surface matte, strong, upper surface color 197A, lower surface color 146D.

Inflorescence description: Does not produce flowers.

It is claimed:

1. A new and distinct cultivar of *Fargesia* plant named 'JAN W2M' as herein illustrated and described.

* * * * *